United States Patent
Rubenstein et al.

(10) Patent No.: US 11,540,787 B2
(45) Date of Patent: Jan. 3, 2023

(54) MEDICAL DEVICES FOR DIAGNOSTIC IMAGING

(71) Applicant: IMAGE INSIGHT, INC., East Hartford, CT (US)

(72) Inventors: Eric P. Rubenstein, Ellington, CT (US); Peter R. Solomon, West Hartford, CT (US); Gordon A. Drukier, New Haven, CT (US); Marek A. Wojtowicz, East Hartford, CT (US); Joseph E. Cosgrove, Columbia, CT (US); Michael A. Serio, Sturbridge, MA (US); James R. Markham, Middlefield, CT (US); Kenneth W. Wang, New York, NY (US); William M. Pramenko, Burke, VA (US)

(73) Assignee: IMAGE INSIGHT, INC., East Hartford, CT (US)

( * ) Notice: Subject to any disclaimer, the term of this patent is extended or adjusted under 35 U.S.C. 154(b) by 0 days.

(21) Appl. No.: 16/927,651

(22) Filed: Jul. 13, 2020

(65) Prior Publication Data
US 2021/0128083 A1 May 6, 2021

Related U.S. Application Data

(62) Division of application No. 16/404,342, filed on May 6, 2019, now Pat. No. 10,751,008, which is a division
(Continued)

(51) Int. Cl.
*G01T 1/24* (2006.01)
*A61B 6/03* (2006.01)
(Continued)

(52) U.S. Cl.
CPC .............. *A61B 6/037* (2013.01); *A61B 6/032* (2013.01); *A61B 6/0492* (2013.01); *A61B 6/107* (2013.01);
(Continued)

(58) Field of Classification Search
CPC ....... A61B 6/037; A61B 6/032; A61B 6/0492; A61B 6/107; A61B 6/4258; A61B 6/481; G21F 5/015
See application file for complete search history.

(56) References Cited

U.S. PATENT DOCUMENTS

| | | | | |
|---|---|---|---|---|
| 2007/0025502 A1* | 2/2007 | Bessho | .................. | A61B 6/032 378/19 |
| 2013/0342851 A1* | 12/2013 | Dresel | .................. | A61B 6/0492 356/601 |
| 2014/0037045 A1* | 2/2014 | Dafni | .................... | G01T 1/2985 378/5 |

FOREIGN PATENT DOCUMENTS

| | | | |
|---|---|---|---|
| JP | 2014202553 A | * | 10/2014 |
| KR | 2010083642 A | * | 7/2010 |

OTHER PUBLICATIONS

Matteson et al., "A directional gamma radiation spectrometer based on pixelated CZT arrays and coded mask apertures," 2006, IEEE Nuclear Science Symposium Conference Record, vol. N06-6, pp. 87-92. (Year: 2006).*

(Continued)

*Primary Examiner* — Kiho Kim
(74) *Attorney, Agent, or Firm* — Troutman Pepper Hamilton Sanders LLP

(57) ABSTRACT

A medical imaging system for detecting ionizing radiation. The system includes one or more pixilated imagers positioned to acquire patient image data and one or more position sensors positioned to acquire patient position data. Once the patient image data and patient position data are
(Continued)

acquired, one or more processors operably connected to each of the one or more pixilated imagers and one or more position sensors calculate a three-dimensional mass distribution based on patient image data and patient position data.

20 Claims, 8 Drawing Sheets

Related U.S. Application Data of application No. 15/590,751, filed on May 9, 2017, now Pat. No. 10,278,656.

(60) Provisional application No. 62/333,754, filed on May 9, 2016.

(51) Int. Cl.
| | |
|---|---|
| *A61B 6/04* | (2006.01) |
| *A61B 6/10* | (2006.01) |
| *A61B 6/00* | (2006.01) |
| *G21F 5/015* | (2006.01) |

(52) U.S. Cl.
CPC ............ *A61B 6/4258* (2013.01); *A61B 6/481* (2013.01); *G21F 5/015* (2013.01)

(56) References Cited

OTHER PUBLICATIONS

Ziock et al., "Source-Search sensitivity of a large-area, coded-paerture, gamma ray imager," IEEE Transactions on Nuclear Science , vol. 53, No. 3, pp. 1614-1621. (Year: 2006).*

* cited by examiner

MEDICAL DEVICES FOR DIAGNOSTIC IMAGING

CROSS-REFERENCE TO RELATED APPLICATIONS

The present application is a divisional application of U.S. patent application Ser. No. 16/404,342 filed on May 6, 2019, entitled "MEDICAL DEVICES FOR DIAGNOSTIC IMAGING," which is a divisional application of U.S. patent application Ser. No. 15/590,751 filed on May 9, 2017, and titled "MEDICAL DEVICES FOR DIAGNOSTIC IMAGING," which claims priority under 35 U.S.C. 119(e) to the filing date of U.S. Provisional Patent Application 62/333,754 filed, May 9, 2016 entitled, "DEVICES FOR MONITORING THE DELIVERY OF RADIO-ISOTOPE TAGGED THERAPEUTIC DRUGS; DIAGNOSTIC IMAGING; AND FOR REAL-TIME DOSIMETRY FOR OCCUPATIONAL AND PERSONAL HEALTH AND SAFETY APPLICATIONS FROM RADIOACTIVE MATERIAL AND IONIZING RADIATION GENERATING DEVICES," the contents of which are incorporated herein by reference in their entireties.

BACKGROUND

A majority of research in medicine takes advantage of radiotracers for the identification of areas to which tagged drugs travel in the body. Where the drug is and when it is there, are critical pieces of information for scientists developing new drugs and applications. When treating patients with radiotherapeutic medications designed to treat a local target area of the body, there is often a need to know the medication's total dose received by the target area, as well as the dose received by other, undesired areas. The dose can be controlled by the rate at which the medication is concentrated in the target area and the rate at which it is dissipated. For medications that are radioactive or have a radioactive tag, concentration and dissipation can be determined by local measurements of radioactivity. For example, if a radio-tagged medicine designed to treat deep-vein thrombosis (DVT) were used in conjunction with a bed containing sensors, real-time computed tomography would allow for assessment of treatment. This assessment may improve medical outcomes by allowing medical staff to administer the smallest dose that provides therapeutic value, potentially reducing complications arising from side effects of drugs, while also monitoring potential side effects from the dose received by other parts of the body. The ability to monitor where the drug is at all times is a key knowledge point.

SUMMARY OF INVENTION

Various embodiments are directed to a medical imaging system or device including one or more pixilated imagers positioned to acquire patient image data; one or more position sensors positioned to acquire patient position data; one or more processors operably connected to each of the one or more pixilated imagers and one or more position sensors, the one or more processors being configured to calculate a three-dimensional mass distribution based on patient image data and patient position data.

In some embodiments, the one or more processors is configured to detect radiopharmaceuticals using the patient image data. IN particular embodiments, the system may further include a mounting apparatus on which the one or more pixilated imagers and one or more position sensors are mounted, and in some embodiments, the one or more pixilated imagers and one or more position sensors can be movable on the mounting apparatus. In certain embodiments, each of the one or more pixilated imager, one or more position sensor, or combinations thereof can be individually attached to a mounting apparatus.

In some embodiments, the system may further include a platform positioned to allow acquisition of patient image data, and the platform may be a table, a bed, or a chair. IN certain embodiments, at least one of the one or more position sensors can be mounted on the platform.

In various embodiments, each of the one or more pixilated imagers may individually be selected from the group consisting of photodiodes, color imagers, monochrome imagers, low light imagers, infrared (IR) imagers, thermal imagers, carbon-metal-oxide semiconductor (CMOS) imagers, and charge-coupled device (CCD) imagers, and in various embodiments, the position sensors may be selected from the group consisting of temperature sensors, piezoelectric pressure transducers, MEMS sensors, and capacitive contact-detection technology.

Further embodiments are directed to a radiation detection system, including a radiation adsorption bed; an air inlet; an air outlet; and a pump operably connected to the air inlet or air outlet configured to create a flow of ambient air through the air inlet, over the radiation adsorption bed, and out the air outlet. In various embodiments, the radiation adsorption bed comprises an activated-carbon sorbent. In some embodiments, the system may further include a temperature sensor positioned to measure an internal temperature of the system, and in some embodiments, the system may further include a heating element operably coupled to the temperature sensor and configured to heat the adsorption bed based on the internal temperature of the system. IN particular embodiments, a processor may be operatively coupled to the temperature sensor and a network connection device and configured to store the internal temperature of the system in at least one of a local storage device and a remote storage device. In some embodiment, the system may further include a radiation monitor positioned to measure a radiation level in the radiation adsorption bed, and in particular embodiments, a heating element may be operably coupled to the radiation monitor and configured to heat based on the radiation level of the system. In some embodiments, the heating element may raise the temperature of the radiation adsorption bed to about 60° C. and about 150° C.

The system of various embodiments, may include a housing encompassing the radiation adsorption bed, air inlet, air outlet, and pump, and in some embodiments, the housing may be configured as a wearable device.

Other embodiments are directed to a wearable radiation detection system, including a housing; one or more pixilated imager chips located within the housing; one or more processors operably connected to each of the one or more pixilated chips, the one or more processors being configured to detect radiation using patient image data.

DESCRIPTION OF DRAWINGS

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

DETAILED DESCRIPTION

Figure 1:
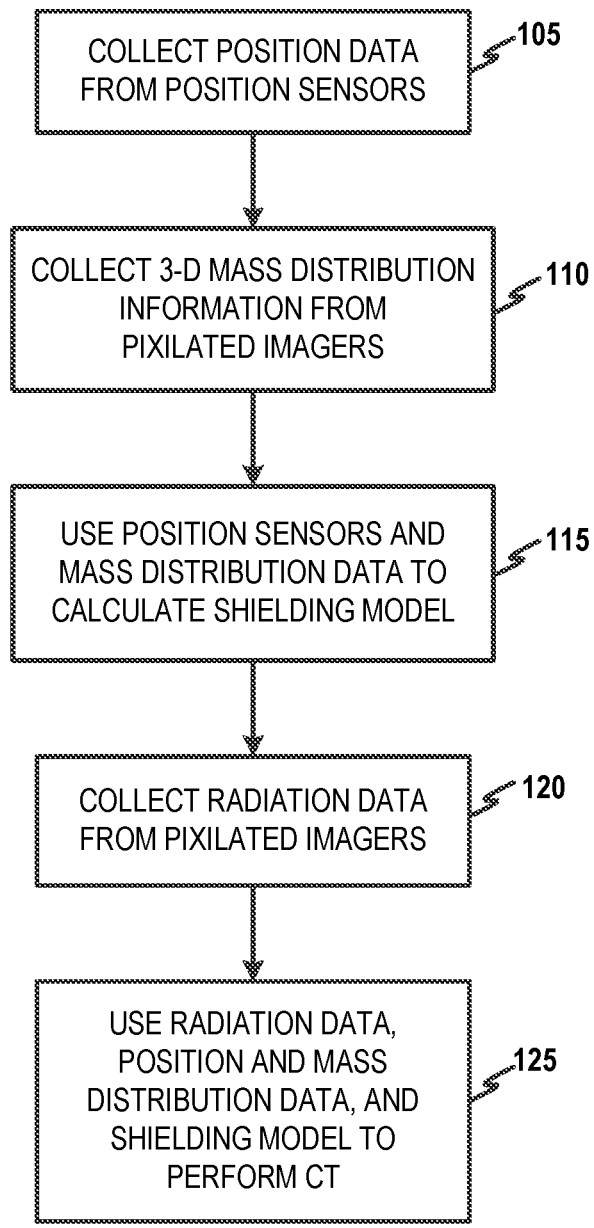
FIG. 1 depicts an illustrative method of data collection of an embodiment.

The above summary of the present invention is not intended to describe each illustrated embodiment or every possible implementation of the present invention. The detailed description, which follows, particularly exemplifies these embodiments.

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

For purposes of the description hereinafter, the terms "upper," "lower," "right," "left," "vertical," "horizontal," "top," "bottom," "lateral," "longitudinal," and derivatives thereof shall relate to the orientation of embodiments disclosed in the drawing figures. However, it is to be understood that embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

It is to be understood that the disclosed embodiments may assume various alternative variations and step sequences, except where expressly specified to the contrary. It is also to be understood that the specific devices and processes illustrated in the attached drawings, and described in the following specification, are simply exemplary embodiments.

1. Medical Imaging

Various embodiments are directed to medical imaging devices for carrying out tomography and methods for medical imaging. The devices and methods use ubiquitous digital cameras to detect ionizing radiation from radiopharmaceuticals for the identification of areas to which tagged drugs travel in the body. Where the drug is and when it is there, are critical pieces of information for scientists developing new drugs and applications. When treating patients with radiopharmaceuticals designed to accumulate in a target area of the body, it is often necessary to know the medication's total dose received in the target area, as well as the dose received by other, undesired areas. The dose received can be determined by the rate at which the medication is concentrated in the target area and the rate at which it is dissipated. For medications that are radioactive or have a radioactive tag, concentration and dissipation can be determined by local measurements of radioactivity.

Embodiments of the invention include methods, devices, and systems in which with one or more image capture devices containing pixilated imagers, position sensors, and processing devices to perform real-time computed tomography that allows for real-time imaging and assessment of treatment. In certain embodiments, the methods, devices and systems may be used in conjunction with radiopharmaceuticals to improve contrast of various body part. This assessment may improve medical outcomes by allowing medical staff to administer the smallest dose that provides imaging or therapeutic value, potentially reducing side effects of drugs. The ability to monitor where the drug is at all times is a key knowledge point.

As used herein, the systems of embodiments can be referred to as devices and vice versa. Thus, the systems of various embodiments include the same components as the devices described below.

Such devices and systems may include one or more pixilated imagers positioned to acquire patient image data. The pixilated imagers may by positioned by any means. For example, in some embodiments, the pixilated imagers can be mounted on a bed, table, chair, or other apparatus on which the patient is placed for imaging, and in other embodiments, the pixilated imagers can be mounted on a mounting apparatus arranged around a bed, table, chair, or other apparatus on which the patient is placed for imaging. In certain embodiments, the pixilated imagers may be movable while mounted on the mounting apparatus. In some embodiments, the pixilated imagers can be moved and repositioned by hand to, for example, focus imaging on a particular part of the patient's anatomy such as a leg, arm, torso, head, and the like and combinations thereof. In some embodiments, the pixilated imagers can be associated with motors or actuators that move the pixilated imagers in patterns dictated by a computer or processing unit associated with the device. In other embodiments, each of the one or more pixilated imagers can be individually attached to a mounting device such as a tripod that a technician positions before imaging commences. In still other embodiments, the one or more pixilated imagers can be mounting on walls of a room in which imaging takes place. In such embodiments, the imagers can be movable by hand or by motors or actuators associated with each imager, and movement can be dictated by a processor.

In some embodiments, the imaging devices may further include one or more position sensors. Like the pixilated imagers, the one or more position sensors can be positioned by any means. For example, in some embodiments, the position sensors can be mounted on a bed, table, chair, or other apparatus on which the patient is placed for imaging, and in other embodiments, the position sensors can be mounted on a mounting apparatus associated with the a bed, table, chair, or other apparatus on which the patient is placed for imaging. In still other embodiments, the position sensors can be mounted on walls of a room in which imaging takes place. In such embodiments, the position sensors can be moveable by hand or by motors or actuators to aid in focusing on a particular part of the anatomy of the patient under study, and movement of the position sensors can be dictated by a processor associated with the device.

The imaging device may generally include one or more processors operably connected to each of the one or more pixilated imagers and one or more position sensors. The one or more processors being configured to calculate a three-dimensional mass distribution based on patient image data acquired from the one or more pixilated imagers, patient position data acquired from the one or more position sensors, or combination thereof. For example, in some embodiments, two or more sensors may acquire pressure and temperature data from the patient. The processor may use this data with information related to the actual, known position of the position sensors relative to each other and use image data to produce a two or three-dimensional image of the patient. Simultaneously, the processor may acquire data related to the position and concentration of radiopharmaceutical in the imaged area using the methods discussed below, and overlay this data on the image to show the location and concentration of radiopharmaceutical in the imaged area of the patient.

In some embodiments, such imaging can be carried out on a particular part of the patient's anatomy such as a leg, arm, torso, abdomen, head, and the like to provide two or three dimensional images of the body part including the concentration and location of a radiopharmaceutical. In other embodiments, such imaging can be carried out on the entire body of the patient. Images acquired from full-body imaging can be used to compare the concentration of radiopharmaceutical in various parts of the body to identify anatomical anomalies throughout the entire body and the compare, for example, the size and location of such anomalies. For example, images and position data can be acquired after administering a radiopharmaceutical designed to detect deep vein thrombosis of a patient's leg to locate blood clots in the vasculature of that leg. In other embodiments, imaging and positioning of the patient's whole body may identify additional blood clots in, for example, the vasculature of untreated leg or arms, lung, or brain. The imaging and positioning data can further provide information relating to the relative size and density of the blood clots identified in various parts of the patient's body. Such information may allow physicians to determine the type of treatment necessary, overall condition of the patient, criticality of treatment, and develop an informed timeline for treating the patient.

The various embodiments are not limited to a particular type of pixilated imager. For example, the pixilated imagers can be photodiodes, color imagers, monochrome imagers, low light imagers, infrared (IR) imagers, thermal imagers, carbon-metal-oxide semiconductor (CMOS) imagers, charge-coupled device (CCD) imagers, and the like and combinations thereof, including imager containing silicon-germanium, germanium, silicon-on-sapphire, indium-gallium-arsenide, cadmium-mercury-telluride or gallium-arsenide substrates and the like, or combinations thereof. In some embodiments, raw video data can be captured by an ensemble of three-dimensional structure scanning sensors. Examples of structure scanning sensors could include one or more of the following used individually or in combination: video or still-image cameras, ultrasonic rangefinder, or other types of devices that identify the physical location of the subject. In some embodiments, the pixilated imagers can include optics such as lenses and focusing apparatuses necessary to focus the imager and created images. The imagers can be configured to take still images, continuous video images, or combinations thereof. For example, in some embodiments, the pixilated imagers can acquire video images of the patient, and still images at certain points during the procedure such as, for example, particular time points identified by the user, when the radiopharmaceutical reaches a particular concentration at a location in the body, or combinations thereof. The pixilated imagers can be arranged to focus on an individual part of the patient's anatomy or the patient as a whole, and in some embodiments, the imagers can be movable by hand or automatically as dictated by a processor associated with the device. In some embodiments, the pixilated imagers may include a pixilated chip without optics or focusing apparatuses and position sensor data can be used to determine the location of the radiopharmaceutical in the patient's body, produce images of the patient, and combinations thereof.

The positions sensors can include, for example, temperature sensors, piezoelectric pressure transducers, MEMS sensors, capacitive contact-detection sensors, accelerometers, and the like and combinations thereof. The position sensors may generally acquire position data through the procedure, and can be arranged to acquire position data for an individual part of the patient's anatomy or the patient as a whole. In some embodiments, the position sensors may individually be operably connected to the processor, and in other embodiments, the position sensors may be operably linked to each other and/or to additional positioning apparatuses such as GPS or other location means.

Data from the position sensors and pixilated imagers mounted at specific designated locations on the device or in a treatment room are used to determine the precise location and distribution of the subject's body. The location and physical distribution information are used to support calculations in order to increase the precision of the results. The use of pixilated imagers arranged in multiple fixed-planes and/or conformal manifolds further increases the precision of the calculations and results. To obtain these data, additional planes of sensors are used on one or more sides of the patient. Although a full box surrounding a patient may or may not be used, each additional sensor adds numerous baselines to the calculations, potentially increasing the value of the data, and the degree of localization achieved. Where localized temperature is needed, additional sensors or thermal IR pixilated imagers are used.

In further embodiments, the devices described above can be combined with traditional computer tomography (CT) devices, position emission tomography (PET) devices, magnetic resonance imaging (MRI) devices, single-photon emission computerized tomography (SPECT) devices, ultrasound devices, and the like. Such devices can include pixilated imagers and position sensors, and processors associated with these devices can be used to produce detailed images of the patient and more precisely located radiopharmaceuticals and other tracers. For example, potential orthogonal measurements can be made using digital imager-based sensing devices that can help confirm or confound the functional assessment by PET. A key functionality of the platform is to integrate heterogeneous data sets from other sensors integrated in real time using the camera-imager-based detection device to collect and transmit information to a central processing unit.

In some embodiments, the imaging devices described above can be used in conjunction with surgical interventions to aid the surgeon in locating abnormalities in the patient. For example, the devices of embodiments can be used with a gamma-knife/gamma-scalpel surgery, a type of radiation therapy used to treat tumors and other abnormalities. The imagers of various embodiments can permit medical staff to monitor the application of treatments in situ and in real time as an independent safety system that could issue an alarm in the event excessive dose is inadvertently delivered. The devices may also provide real-time treatment information to confirm the delivery of therapeutic levels of radiation. Such real-time monitoring could serve as a permanent record of the therapy, enabling doctors to plan future treatments with the goal of minimizing delivered dose to healthy tissue while maximizing dose to the tumor. It would also be a valuable source of data for researchers seeking to improve the medical standard of care that is not currently available.

Further embodiments are directed to wearable imaging devices having incorporated one or more position sensors and, in some embodiments, one or more pixilated imagers. For example, in some embodiments, articles of clothing, such as pants, shirts, headwear, coveralls, or pajamas incorporating one or more positions sensors may be used in combination with mounted pixilated imagers in devices such as those described above, and image, position, and location of radiopharmaceutical data acquired from these devices can be used to create detailed images of the patient and the locations and concentration of radiopharmaceutical in various locations in the patient's body. In other embodiments, the one or more position sensors can be incorporated into a blanket that is used to cover the patient during imaging.

In other embodiments, the one or more pixilated imager may be incorporated into the article of clothing or blanket. In such embodiments, the pixilated imagers can identify the location and concentration of radiopharmaceuticals while the position sensor data is used to produce a two or three-dimensional image of the patient. In some embodiments, the pixilated imagers may include optics and focusing apparatus, and in other embodiments, the pixilated imagers may be a pixilated chip with no optics or focusing apparatus.

Additional embodiments include methods for using the devices described above to produce tomographic images of the patient or to locate radiopharmaceuticals or therapeutic radiation in the body of a patient. For example, in some embodiments, as illustrated in the flow diagram FIG. 1, position data acquired from position detectors such as pressure sensors 105, and image data acquired from pixilated imagers 110 can be used to produce a mass distribution and patient position information combined with the position and pressure sensor data to calculate a shielding model 115. Radiation data may be collected from the one or more pixilated imagers or pixilated chips 120 and these data may be combined with calculated shielding model to perform tomography 125. The steps provided above can be carried out in essentially any order. For example, in some embodiments, radiation detection 120 can be carried out in a first step and position and pressure sensor data can be used to calculate a shielding model 105, 110, 115 of only portions of the patient's body that emit radiation at a particular level.

Figure 2:
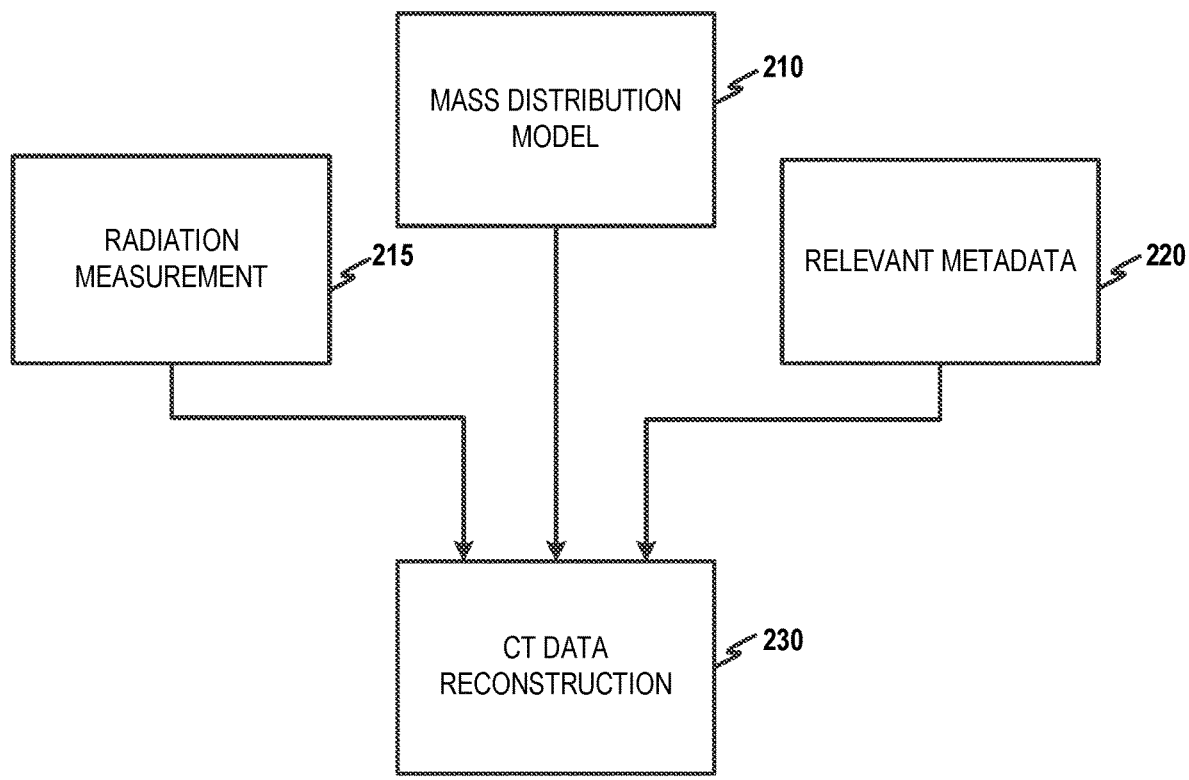
FIG. 2 depicts an illustrative method of data processing for various steps of an embodiment.

As illustrated in the flow diagram of FIG. 2, in some embodiments, different processors can carry out data processing for various steps of the methods simultaneously and the processed data can be combined by a central processor. For example, a mass distribution model can be created from image data and position center data at one processor 210, radiation measurements can be determined in another processor 215, and relevant meta-data can be compiled in another processor 220. These data can be compiled and used to create CT data reconstruction 230 in any one of the processors used in the preceding steps or in another processor.

In some embodiments, the radiation data can be collected and analyzed by data-processing boards, which may be single-board computers (SBC), digital signal processors (DSP), field programmable gate array (FPGA) processor boards, general-purpose computers, or specially designed processing components. The sensors may be embedded on computing devices (middle tier) or flow data to a processor that is physically distinct or even distant. Once the processors make and quantify each radiation measurement, the resulting readings can be sent to another processor, which collects and collates these measurements with associated meta-data. The meta-data may include, for example, the subject's location, the temperature of the sensor to characterize signal and noise characteristics, amplifier settings to characterize signal and noise characteristics, the sensor's identification code to keep track of differing sensor characteristics, the type of sensor (e.g. ELP-USB30W02M-L21 CMOS sensor or OV6211 CMOS sensor, a Cesium-Iodide crystal based detector, etc.), and other similar meta-data. The data and meta-data can be stored and made available for subsequent sensor-fusion and analysis.

In another embodiment, the collection of the physical location and physical extent of a subject can be used to improve computed tomography calculations. Multiple detectors may be positioned and aimed to capture the location and physical extent (i.e. size) of the subject. The subject may be simultaneously imaged by several pixilated imagers that surrounding the subject. Image processing software can be used to perform feature detection, identification of common features, image registration, and calculation of trigonometric parallax. From this information a three-dimensional model can be developed that mimics the subject's physical extent. Since this mathematical model is tied to the subject's physical body, a detailed model is built that incorporates body structures (e.g., musculo-skeletal and organ structures). This model can then be used to add constraints to the CT calculations to improve the calculations for the source and shielding terms.

In some embodiments, 3-D structure data can be collected by pixilated imagers (bottom tier) and analyzed by data-processing boards (middle tier), which may be single-board computers (SBC), digital signal processors (DSP), field programmable gate array (FPGA) processor boards, general-purpose computers, or specially designed processing components. The sensors may be embedded on compute devices or flow data to a processor that is physically distinct or even distant. Once the processors make and quantify each 3-D measurement, the resulting readings are sent to another processor, which collects and collates these measurements with associated meta-data. The meta-data may include: the subject's location, the scanner's location, the temperature of the sensor to characterize signal and noise characteristics, amplifier settings to characterize signal and noise characteristics, the sensor's identification code to keep track of differing sensor characteristics, the type of sensor (e.g., video camera, LIDAR, RADAR, etc.), and other similar meta-data. The data and meta-data are stored and made available for subsequent sensor-fusion and analysis that incorporates other position data. This analysis can build a full 3-D model that contains locations of key components (e.g., bones, heart, bladder, thyroid gland, etc.) as well as the composition of those structures. This combined digital model will be used as input.

In further embodiments, the results of the radiation measurements over time and location can be fused with the detailed mass-distribution model. Associated subject meta-data informs the details of the CT reconstruction. The resulting computed image makes use of all available data to achieve a cost-effective time-tagged, 3-dimensional representation.

In some embodiments, the systems and devices described above may include one or more mobile devices having a display, a processor, a location-aware component (for example, Global Positioning Satellite ("GPS") component, a wi-fi location component, indoor positioning system capability, and a means for communicating with processor, and in certain embodiments, the processor may be operably connected to other computing devices, such as, for example, a server. Each mobile device may be configured to communicate with a processor via a network, such as, for example, the Internet, an intranet, a wide area network, a metropolitan area network, a local area network, an internet area network, a campus area network, a virtual private network, a personal network, and the like and combinations thereof. For example, the processor may communicate digital still or digital video images to the mobile device, and the mobile device may transmit commands to the processor to, for example, provide images of a particular body part of the patient or focus the one or more imagers on a particular location. A user having access to the mobile device may control all or some of the aspects of the device throughout use.

Table 1 provides various examples of certain types of imaging that can be carried out using the devices describe above.

| Disease | Imaging agent | Functional assessment | Principle | Potential orthogonal measurement |
| --- | --- | --- | --- | --- |
| Cardiac | FDG | Myocardial metabolism at rest, measure fatty acid uptake by the myocardium | Differentiate between ischemic, viable myocardium and necrotic, scarred myocardium | Visual Cardiac markers in blood |
| | FDG | Myocardial perfusion | In compromised myocardium, uptake of FDG indicate viability and likely positive response to myocardial revascularization | Visual Cardiac markers in blood |
| | $^{11}$C-MQNB | Receptor density | Congestive heart failure is associated with an up-regulation of myocardial muscarinic receptors | |
| | FDG | Presence of arterial plaque | FDG uptake correlates with macrophage accumulation and inflammation. | |
| Vascular | FDG | Effectiveness of device or drugs in reducing plaque | Therapy with anti-inflammatory agents in arterial vasculature reduces plaque FDG uptake. | Visual Cardiac markers in blood |
| Cancer | FDG | Diagnosis, staging and detection of metastatic disease | Higher FDG uptake by tumors | Panels for cancer markers |
| | FDG | Prognostic information based on response to therapy | | |
| Infectious - HPV | FDG | Nodal PET/CT parameters predict HPV status | High nodal FDG uptake should raise suspicion for positive HPV status | Fluorescent biomarker |
| Neurological | florbetapir F-18 Amyvid | Estimate of amyloid neuritic plaque density in different regions of the brain | Glucose transport is up-regulated in diseased tissue | |
| | florbetapir F-18 Amyvid | Dose response of new drug candidates designed to | Increasing dosages of drug candidates remove increasing amounts of plaque associated with Alzheimer's disease | |

Various improvements on existing technology can be obtained using the devices and methods described herein. For example, in some embodiments, higher spatial resolution determinations of the location of radioactive materials and enhanced angular resolution of the resultant tomographic reconstruction of source material distribution beyond the current technology can be obtained. Embodiments include several techniques that can increase the resolution compared to simply using the average 3-dimensional location of each image sensor as a location node in the tomographic reconstruction. For example, more than one pixilated imager or pixilated chip can be used in a specific location, thereby breaking sensitivity degeneracies. Shielding can be employed to preferentially occlude certain regions, yielding an effect similar to "coded aperture" techniques. Individual chips or clusters of chips can be placed inside of boxes or cylinders that are open (unshielded) in only one direction, greatly reducing the solid-angle that is effectively contributing to the overall reconstruction. Algorithms can be used to compute the direction of origin of each gamma ray from its on-chip energy distribution. In certain embodiments, combinations of these techniques can be incorporated into the device. These techniques are described in more detail below.

Multiple chips in one place—Placing multiple detectors near one location in the distribution of detectors gives two advantages to the system. Locally, they enhance sensitivity by providing more detector volume and thereby geometric gain. This effect is proportional to the square root of the number of equivalently sized detectors. More importantly, with strategically chosen spacing at various locations, the additional number of baselines obtained by combining multiple, nearby pairs, increases the spatial resolution that can be achieved in the CT analysis. The ability to improve the spatial resolution of source terms between sets of multiple detectors will also improve contrast data for overall image quality improvement.

Coded-aperture-like shielding—For large, single detectors, or arrays of detectors, at a location, a suitably constructed mask made of lead or a similar radiation-blocking material can be used to occlude certain portions of the field of view from these detectors. In this case, the distribution of radiation detections on the detector can then be used to recover directional information regarding the origin of the gamma rays.

Use of shielded boxes/cylinders to occlude large solid-angles—Similar to the above, in this case the detector or detectors are partially enclosed in an enclosure made of lead or a similar ionizing radiation-blocking material. For example, by placing a detector in an open cylinder or cone, the sensor's sensitivity to off-axis radiation is diminished, whereas normally the detectors are sensitive to ionizing radiation coming from all directions. By so enclosing them, the direction from which detected ionizing radiation could be coming is restricted. This additional information can then be used in assessing the spatial distribution of ionizing radiation sources within the field of interest. This effect is particularly significant when using relatively lower energy radiation, e.g. less than ~250 keV, which is far less penetrating for bone than higher energy radiation.

Increasing sensitivity or selectivity by temperature modulation or other active sensing—The use of temperature modulation has the potential to enhance the sensitivity or selectivity of pixilated imagers or pixilated chips to gamma rays (or betas). This approach can be used effectively with metal oxide (MOX) sensors for gas mixtures in which the MOX sensor adapts its operating temperature in real time to sequentially reduce uncertainty in the concentration estimates for a gas mixture. This is an example of what is known as active sensing, where the sensor adapts to the measurement environment.

Figure 3:
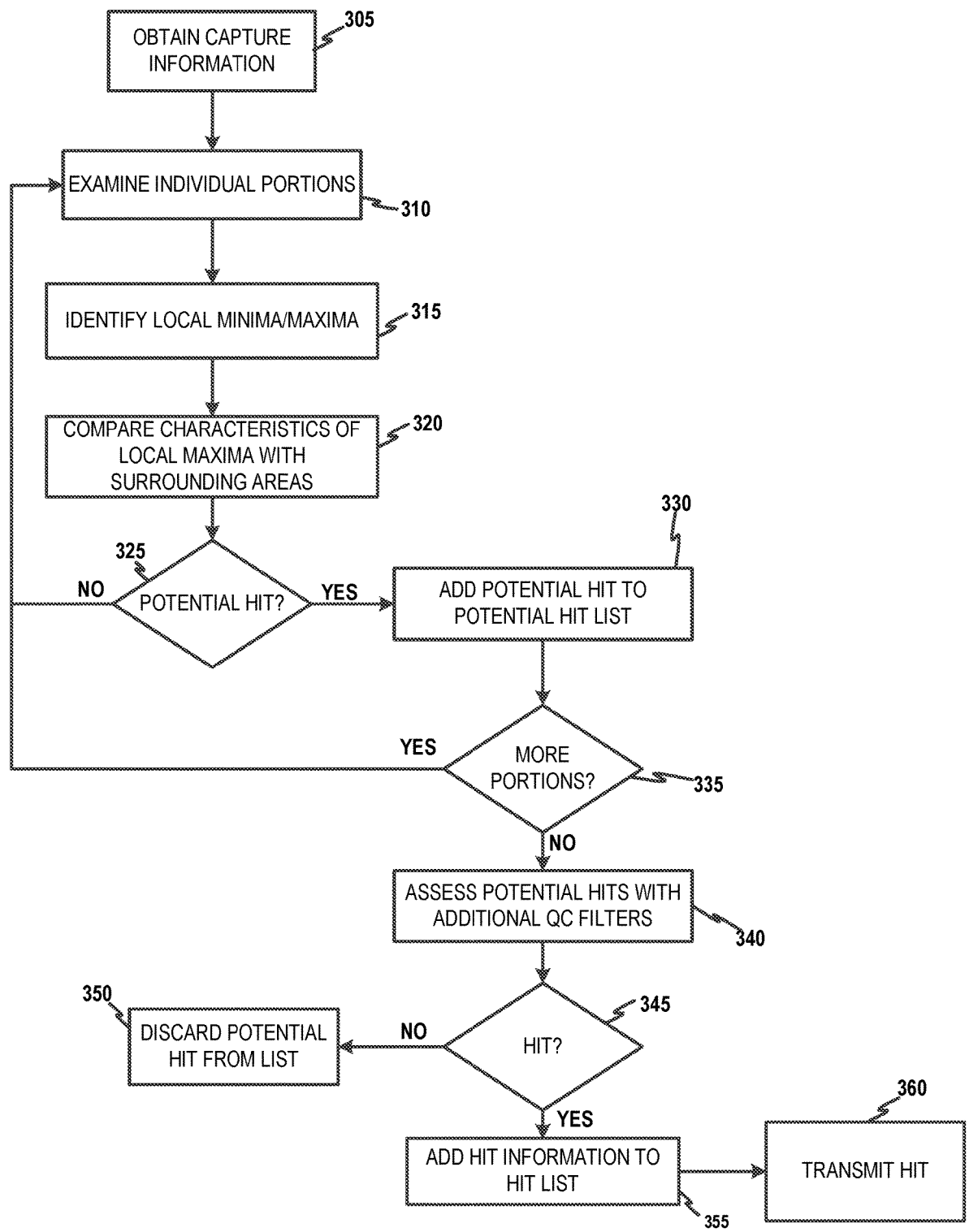
FIG. 3 depicts an illustrative method of detecting potential hits in an embodiment.

In various embodiments described above, radiation may be detected using the method illustrated in FIG. 3. For example, the processor may examine 310 individual portions of the capture information such as, for example, frames within an image and the like to identify 315 local maxima and/or minima. In embodiments in which the pixilated imager is calibrated to detect radiation, the application environment may identify local maxima. As each local maximum is identified 315, the application environment may compare 320 the characteristics of the image pixels comprising the local maximum with any pixels substantially surrounding each local maximum. A wide range of suitable maxima-finding algorithms may be used to compare local maxima with the surrounding pixels. For example, a non-limiting way of comparing may include evaluating the four closest pixels (4CP) in digital image data. If the pixel or image data point under consideration is (X,Y), then the 4CP are: (X+1,Y), (X,Y+1), (X−1,Y), and (X,Y−1). The local background value of the imager may be taken as the average of the eight pixels corresponding to (X−2,Y−2), (X,Y−2), (X+2,Y−2), (X−2,Y), (X+2,Y), (X−2,Y+2), (X,Y+2), (X+2, Y+2). Alternatively, if a known reference object is in the field, it may be set to be the background and the average of the pixels or data points corresponding to the object set to the background.

Based on the captured information and/or the comparison, the application environment may determine 325 whether a potential hit exists. For example, if the local maxima that meet or exceed one or more thresholds may be considered areas that include potential hits for radiation emission. In embodiments where radiation is detected, the thresholds may include total counts in the local maximum, total counts summed over the local maximum plus surrounding pixels, an excess of either of the above-described thresholds with respect to a measure of the average counts in pixels away from any local maximum, ratios of such total counts or excesses to the average, standard deviation, and/or other statistical measures of counts in areas away from a local maximum. If a potential hit exists, the application environment may add 330 the potential hit to a list or enter the potential hit in a database and store information regarding the potential hit for further review. Once a potential hit has been added to the potential hit list, the application environment may determine 335 whether additional portions must still be examined, and if so, may examine 310 the additional portions. In some embodiments, the application environment may repeat the process or identify local maxima or minima meeting lower or higher thresholds, where such adjustments to the thresholds may be determined from the information stored from previously detected potential hits.

If no more frames remain, the application environment may assess 340 each potential hit in the hit list with one or more additional quality control (QC) filters. Examples of additional QC filters may include, but are not limited to, limits on the number of potential hits detected on a single frame, limits on the number of potential hits detected on a single pixel and/or on groups of neighboring pixels, limits on the frequency of potential hits detected on a single pixel and/or on groups of neighboring pixels, comparison to thresholds as previously described herein as may have been adjusted according to the information stored regarding all or a portion of the potential hits in the list or other lists, or a location on the component.

The application environment may determine 345, after assessing 340 each potential hit, whether each potential hit is an actual hit. A potential hit may be determined to be an actual hit if it passes some or all of the additional QC filters. If the potential hit is found to not be an actual hit, the application environment may discard 350 the potential hit from a final hit list, and may optionally adapt dynamic parameters that would update thresholds and/or QC filters. If the potential hit is found to be an actual hit, the application environment may add 355 the potential hit to the final hit list and/or enter the actual hit into a database and store the actual hit. In some embodiments, the application environment may also add 355 information relating to the hit to the final hit list. Examples of information relating to the hit for embodiments in which imagers are calibrated may include, but are not limited to, images, coloration of local maxima pixels, coloration of surrounding pixels, the total number of pixels examined, the total number of frames, the detection parameters associated with the maximum or minimum detection, additional QC filter results, the number of hits that passed the additional QC filter, the number of potential hits that did not pass the additional QC filter, information regarding the initialization results obtained from the initialization, information about the electronic device, information about the components, geolocation information, information regarding a user of the electronic device and the like, or combinations thereof. Examples of information relating to the hit for embodiments related to other components may include baseline magnetic readings (e.g., strength and direction), variability of magnetic readings, various statistical moments of magnetic readings, baseline accelerometer readings, variability of accelerometer readings, various statistical moments of accelerometer readings, temperature readings, variability of temperature readings, various statistical moments of temperature readings and the like, or combinations thereof.

2. Occupational Health and Safety

As discussed herein, radiology is regularly used in medical environments (e.g., hospitals). Generally, the staff or personal in these facilities need to monitor their exposure to radiation. Thus, there is an ongoing need for dosimeters to worn by hospital staff, security personnel, and the like who work near X-ray scanners or devices that put off trace amounts of radiation (e.g., workers who operate near industrial radiography equipment, aircrew, etc.). Accordingly, some embodiments described herein may provide an improvement over current dosimeter technology, (e.g., dosimeter badges) by allowing continuous, real-time readings of ionizing radiation exposure. In addition to radiation exposure levels being recorded, additional user information, such as for example, positional information (e.g., relative to the building they are located in) and time stamping may be recorded to help locate a potential source of radiation exposure. Moreover, the ability to provide data to a Radiation Safety Officer, in real time, as to the exposures being monitored on all workers at potential risk for radiation enables full compliance with even the most strict applicable policies and regulations.

Accordingly, in some embodiments, a radiometer system may be used that includes a small, light-weight sensor. The light-weight sensor may then be in communication with one or more computers (e.g., laptop or server) in order to analyze, store, and transmit the results from the sensor to a secondary system.

In some embodiments, a sensor, (e.g., one or more image capture devices (digital pixelated image sensor)) may be operatively coupled to one or more controllers, one or more digital signal processors (DSP), or other similar computer node. The sensor may be worn by a user as a wearable device (e.g., a badge, a patch, a bracelet, a pendent, etc.). In some embodiments, the sensor may be solo in nature, collecting data and communicating with the one or more controllers or one or more DSP to analyze the data captured by the sensor. Additionally or alternatively, a plurality of sensors may operate in a group (e.g., mesh network, ad-hoc network, a network with a single base station, etc.). By way of a non-limiting example, medical staff who are performing a fluoroscopy procedure may wear multiple sensors (e.g., dosimeters) at key locations on their bodies. In some embodiments, the sensors may be located at an individual's core, at an individual's extremities, and/or at areas considered to be radiation sensitive.

Once the data is collected by the one or more sensors, it may be transmitted as either raw data (e.g., video, long exposure images, etc.) or as reduced data (e.g., determined radiation results) via a wired network connection or wireless network connection (e.g. Bluetooth, Wi-Fi, etc.) to a computing device (e.g., smartphone, tablet, laptop, desktop, server, etc.). In some embodiments, a specific software application (e.g., GammaPix, etc.) may allow a smartphone or other computing device to receive and analyze the images transmitted by the one or more sensors. In addition, in some embodiments, the computing device may store the results, which may then be displayed locally or remotely (e.g., after being transmitted to a remote location, such as the office of an attending physician) for review.

In some embodiments, the systems and devices described above may include one or more mobile devices having a display, a processor, a location-aware component (for example, Global Positioning Satellite ("GPS") component, a wi-fi location component, indoor positioning system capability, and a means for communicating with processor, and in certain embodiments, the processor may be operably connected to other computing devices, such as, for example, a server. Each mobile device may be configured to communicate with a processor via a network, such as, for example, the Internet, an intranet, a wide area network, a metropolitan area network, a local area network, an internet area network, a campus area network, a virtual private network, a personal network, and the like and combinations thereof.

As discussed herein, an image capture device (e.g., one with a pixelated imager) may be used to track or monitor radiation levels. Thus, although personal dosimeters exist, an embodiment, as described herein may allow a personal dosimeter to be constructed from any electronic device that contains a pixelated imager. By way of non-limiting example, a wearable device (e.g., a common wrist-computing device or the like) may capture data and process it onboard using organic compute capabilities (i.e., an embedded processor). Additionally or alternatively, the data may be captured and either partially or wholly processed onboard the wearable device or not processed onboard at all. When the wearable device is not used for the complete processing of the detected data, the wearable device may transmit the intermediate-processed or raw data to an external compute node (e.g., smartphone, tablet, laptop, etc.). That node may be another mobile device, a nearby computer, or a far distant resource. It should be understood by those skilled in the art, that the transition may happen directly (e.g., via Bluetooth) with a device in close proximity, and/or through the use of proxy devices (e.g., a Wi-Fi hotspot and the internet). Thus, the computer device used for processing the information gathered from the wearable sensor may be in close proximity (e.g., a user's smartphone) or extremely far away (e.g., a remote server accessed via the Internet).

In some embodiments, and as discussed herein, a dosimeter (e.g., sensor) may provide real-time data to a remote computer. The remote computer may be located in a stationary office, mobile vehicle, determined command-post, or the like. In a further embodiment, the remote computer may be monitoring and receiving information from a plurality of dosimeter devices (e.g., devices carried by each person on the medical staff). The monitoring of radiation in real time allows for quick and responsive action. For example, if an individual were to receive a sudden increase in dose-rate (e.g., radiation dose rate), or begins to approach their administrative or safety limit, an action can be performed (e.g., alarm can be sound, medical personal may be notified, systems within the proximity of the detection may be shut down to avoid high contamination risks).

Accordingly, in some embodiments, users (e.g., staff) may be warned by an alarm or message sent from the detecting device (e.g., dosimeter) or a remote command post (e.g., smartphone, tablet computer, server, etc.). Although medical applications are discussed herein, alternative uses exist. By way of non-limiting example, embodiments discussed herein may be particularly relevant to an industrial radiography unit, which, for example, may perform non-destructive X-ray evaluation of a structure (e.g., bridge, building, etc.) or transport (e.g., ship, plane, vehicle, etc.).

In some embodiments, as discussed herein, the sensor (e.g., dosimeter), including the housing may be small in size and cost. Thus, not only does the reduced cost of the detector, allow for the possibility of wearing multiple dosimeters on multiple body parts, but the small size (e.g., footprint) allows them to be less intrusive, and thus more likely to be worn. For example, current products make it difficult to identify an extremity dose. However, in some embodiments, the extremity dose can now easily be determined by one or more rings (e.g., smart rings) worn on each finger, all utilizing telemetry.

Once all the sensor data has been collected, calculations may be carried out to determine various factors about the contamination. (e.g., which direction the exposure came from) may be possible in an immediate forensics effort for the Health Physicist. In some embodiments, a camera chip based dosimeter may contain one or more complementary metal-oxide semiconductor (CMOS), semiconductor charge-coupled devices (CCD), or similar image sensors along with camera-control circuitry. It should be understood, that various embodiments are not limited to a particular type of pixilated imager. For example, the pixilated imagers can be photodiodes, color imagers, monochrome imagers, low light imagers, infrared (IR) imagers, thermal imagers, carbon-metal-oxide semiconductor (CMOS) imagers, charge-coupled device (CCD) imagers, and the like and combinations thereof, including imager containing silicon-germanium, germanium, silicon-on-sapphire, indium-gallium-arsenide, cadmium-mercury-telluride or gallium-arsenide substrates and the like, or combinations thereof.

Relevant control circuits would accompany photodiode or other sensors. In one embodiment, the data would be processed locally and results shown to the user and transmitted wirelessly to a database for subsequent processing. In another embodiment, the data would be wirelessly transmitted to a processor for centralized analysis, storage, and monitoring. Additional valuable metrology is collected with embedded sensors such as iBeacon, pressure, accelerometer, magnetometer, and thermometer detectors.

As described herein, many professions require that personnel who work with radioactive sources or ionizing radiation generating devices use a personal dosimeter based upon the likelihood that they exceed exposure limits. However, due to the limitations of current monitoring systems, other personnel who work nearby, but who are not regularly exposed to radioactivity may not actively use dose-monitoring equipment. This non-use may be due to cost measures, or simply that the utility of current dosimeters makes them ineffective for such individuals (i.e., those not regularly exposed to radiation). However, with the real-time monitoring, the additional information gathered by devices in proximity to radiation may still help determine issues or timing of incidents.

Of particular note is the ability of some embodiments to store the time, using a time-tagged exposure record, and optionally store location information associated with the location at which the exposure was logged. As discussed herein, an embodiment may identify an emerging exposure problem before it has a chance to harm anyone, (e.g., a leak from a storage drum that allows radioactive waste to travel from an isolated containment area.)

In additional to ensuring safety measures, an embodiment may also be capable of eliminating fraudulent claims of radiation exposure. Although rare, there are instances where individuals have placed a dosimeter near a known radioactive source for an extended period of time, and then claimed to have received a large dose radiation based on their dosimeter reading. Thus, because, as discussed herein, embodiments capture not just location, but also timing of the exposure, it makes fraudulent claims much easier to identify. This saves an employer money, as it avoids the employee's request for damages, legal fees, lost time, as well as other negative consequences. In order to further strengthen this capability, some embodiments may include one or more of body-temperature sensors, accelerometers, and location monitoring technologies to not only determine exposure rate and time, but also various other factors. By way of non-limiting example, the body-temperature sensor may indicate that a user has removed their wearable dosimeter. If it can be shown that radiation exposure of the dosimeter occurred when the user was not wearing their device (e.g., based on the body-temperature sensor), it may indicate that the user was, in fact, not exposed at the same rate as the dosimeter.

Moreover, if a dosimeter were to be removed from the user's body and placed near a radiation source, the resulting lack of motion (e.g., based on the accelerometer), combined with its location, would make the resulting exposure a good candidate for further investigation—all the more so if an on-board temperature sensor simultaneously detected a substantially lower "body temperature" reading. Because some embodiments tag the exposure location and time, it may also be straightforward for an embodiment to interact with a separate system and to search security video records for nearby locations to verify that the person of interest did not, in fact, remain where the alleged exposure was reported to have occurred.

In addition to monitoring external sources of radiation, the sensor device (e.g., dosimeter) may be used to monitor drug dosage in a patient's body. In some embodiments, a sensor may be worn by the patient as a wearable device (e.g., a patch, a bracelet, a pendent, or other means of attachment), singly or in groups. By way of non-limiting example, radioactive iodine would be expected to concentrate in the thyroid gland. With this knowledge, a sensor device may be placed in an area adjacent or contacting the thyroid gland. Using the dosimeter, a doctor can determine the amount and residence duration of a chemical. Thus, rather than injecting a patient with an average or recommended dose, a doctor may start out using a smaller dose and then assess the resulting concentration of radioactive material actually delivered to the target site. Due to the physiological difference between patients (e.g., size, sex, age, etc.) each person has a unique rate at which they process therapeutic material. Thus, being able to monitor the drug dose accurately and in real time may save many people from receiving an excess dose.

In some embodiments, more than one medicine may need to be administered at a time, and each one could contain (or be) a different isotope that emits varying energy gamma rays. The ability to differentiate gamma rays of different energies (see U.S. Pat. No. 9,000,386) would allow for tracking the source materials separately. The advantages, as discussed herein, of multiple embodiments, are: low cost, light weight, small volume, well calibrated, low power, portability, and low network bandwidth requirements. In addition, as discussed, embodiments may provide continuous monitoring, automatic reading, and automatic reporting to a physician or radiation safety officer.

In a further embodiment, the new proliferation of activity trackers may be utilized for abilities discussed herein. Generally, these activity (fitness) trackers are wearable devices that monitor and record a person's activity level. These trackers may record activity using a variety so sensors (e.g., pedometer, accelerometers, altimeters, etc.). This recorded data can be used to calculate mileage, estimate calorie expenditures, determine sleep quality, and measure heart rate. Additionally, most activity trackers interact with a secondary device (e.g., a smartphone, tablet, etc.) to generate charts and/or graphs that display the monitored physical activity, food consumption, water consumption, etc. As their capabilities improve, additional technology, such as that disclosed herein may be included. By way of non-limiting example, GammaPix technology could be included in a wearable device/smartphone combination in order to measure the gamma and beta radiation exposure of an individual.

In addition to gamma and beta radiation, embodiments may be able to detect radon and other radioactive gases. In at least one embodiment, continuous measurement of ionizing radiation caused by radon and other radioactive gases may be monitored and recorded. For example, for radon, Rn-222 and its associated solid daughter products polonium, bismuth, and lead all emit gamma rays that are easily measured by the system.

According to the U.S. Environmental Protection Agency (EPA), radon is a leading cause of lung cancer among non-smokers, and it is responsible for more deaths than second-hand smoking. While radon is regulated to 4 pCi/l of ambient air, the daughter products contribute most of the undesired dose to lungs. Thus, an embodiment may measure the threat level and may show compliance with radon requirements. Radon is invisible, has no smell, and the only way to know one's exposure to radon is through testing. Currently, testing for radon is insufficient because, test procedures do not provide a continuous measurement and, thus, they need to be periodically repeated. Moreover, the current systems require handling, including mailing test kits to a laboratory, which can take days, weeks, or months depending on the test duration. Finally, adsorption temperature is not monitored or controlled, during the measurement, and it is well known that adsorption equilibrium is strongly temperature dependent.

Thus, some embodiments, as discussed herein, provide active measurement for measuring gamma and beta radiation resulting from the presence of radon or other radioactive gases. The active measurement may be provided based on radon adsorption on activated carbon and the associated de-sorption. However, unlike current methods, the measurement is continuous, and device operation is fully automated and unattended, including spent-carbon regeneration.

In addition, it is possible to record and monitor results on an on-going basis, either through a web-based app or any other suitable data logger. In some embodiments, a flow of air is forced through a bed of carbon material by a small pump (i.e., forced convection), thus, the measurement time is shorter than in the case where the air slowly diffuses into charcoal particles. Furthermore, it is in principle possible to eliminate or reduce gas humidity in a flow system, (e.g., by means of the appropriate drying unit placed upstream of the radon detector). Finally, the adsorption temperature is measured, and can thus be controlled and/or accounted for, so that the amount of radon detected in the carbon can be reliably related to radon concentration in the gas phase.

Figure 4:
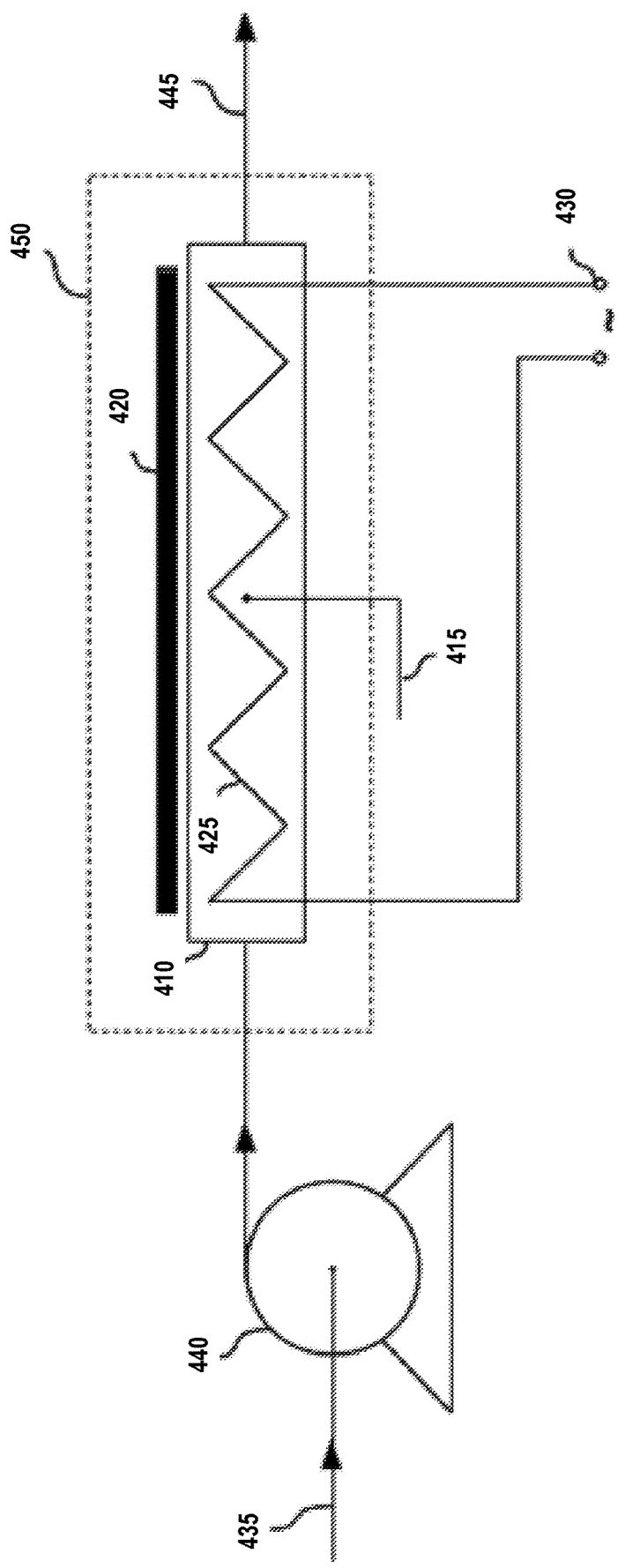
FIG. 4 depicts a schematic representation of an illustrative continuous monitoring device for measurement of ionizing radiation.

As shown in FIG. 4, an embodiment may have a bed of activated carbon sorbent 410 where radon adsorption takes place. In some embodiments, ambient air 435 may be forced through the carbon bed 410 using a pump 440. Once the ambient air 435 moves across the carbon sorbent 410 it may then exit the system through one or more air outlets 445. In some embodiments, the temperature is monitored using a thermocouple or like device 415, and the continuous or semi-continuous radiation measurement is provided by means of a suitable ionizing radiation monitor 420 (e.g., a digital CMOS camera coupled with the GammaPix software). Additionally or alternatively, the sorbent material 410 may be enclosed in a temperature-controlled enclosure 450. In further embodiments, the saturated (e.g., partially saturated) sorbent 410 may be periodically regenerated by thermally desorbing radon into the flow of air 435. This regeneration is effected by the heating element(s) 425 and the power supply 430. In some embodiments, the entire operation may be fully automated and controlled by an information handling device (e.g., micro-computer, microcontroller, processor, etc.). Thus, as discussed herein the radon-enriched exhaust may be vented outside of the structure being monitored.

Radon monitoring is generally related to homes and the sale of homes. Thus, there may be circumstances where a radon measuring device is in use while a property is occupied by individuals (e.g., homeowners, rents, potential purchasers, etc.). In order to ensure a home passes the test, a homeowner may be a tempted to move the radon-measurement device to an upper floor of the home, which typically has very low radon levels. Thus, some embodiments may include a motion sensor and/or location-monitoring equipment (e.g., accelerometers, GPS, GLONASS, iBeacon, etc.). IBEACON is a registered trademark of Apple Inc., in the United States of America and other countries. The location monitoring electronics may add protection against corrupt or incorrect measurements by detecting and storing information related to device movement. Another potential risk is that outside air may be blown (e.g., accidentally by an HVAC unit or on purpose by an individual to manipulate the test) into the space to be monitored. The addition of additional air could greatly dilute any radon adsorbed by the activated carbon sorbent, and thereby corrupt the measurement. However, as discussed herein, some embodiments may include a thermometer to measure the ambient temperature in the device. Measuring the temperature around the activated carbon may provide some protection from efforts to blow outside air into the controlled space (e.g., a basement) as such efforts will usually generate a perturbed temperature record.

Figure 5:
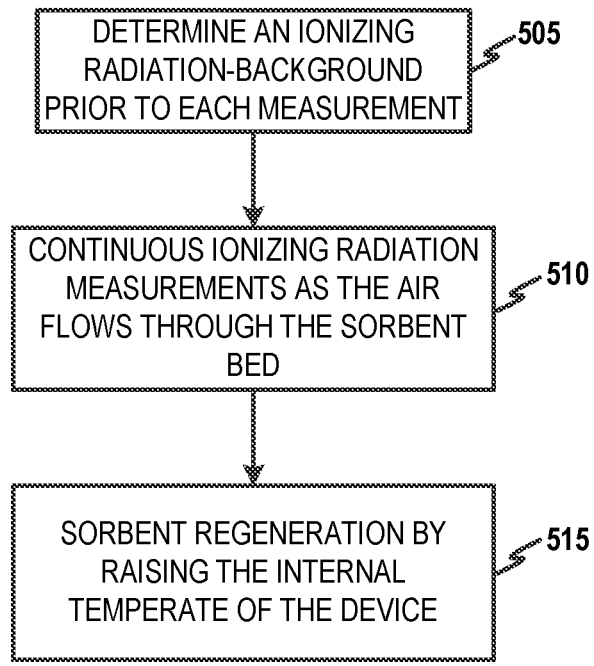
FIG. 5 depicts an illustrative method of continuous monitoring device for measurement of ionizing radiation.

Accordingly, as shown in FIG. 5, embodiments as discussed herein may determine an ionizing radiation background prior to each measurement 505. In some embodiments, this process is performed when no gas-flow is occurring, immediately after the carbon bed has been regenerated. In further embodiments, the measurement is performed for a period of time sufficient to characterize the ambient radiation level to a statistically-significant degree. Once the radiation-background is determined 505, an embodiment may perform continuous ionizing radiation measurements as air flows through the sorbent bed 510. As the airflow passes through the system, the ionizing radiation and temperature data are detected and recorded. As discussed herein, these measurements may be recorded locally, or transmitted to a remote storage device (e.g., a server, smartphone, tablet, laptop, etc.). As further discussed herein, if temperature, location, and/or acceleration of the device is detected and appears erroneous, alerts or alarms may be triggered to inform a user of potential errors or tampering. In further embodiments, separate barometric pressure and humidity sensors may be used, and similar to the above, tracked rerecorded and stored (e.g., locally or remotely). Once the system described in various embodiments herein is functional for a period of time, it may be required to regenerate the sorbent. Thus, some embodiments may regenerate the sorbent by raising the internal temperature of the device 515.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including LAN or WAN, or the connection may be made to an external computer (for example, through the Internet using an Internet Service Provider).

Aspects of the present invention are described herein with reference to flowchart illustrations and/or block diagrams of methods, apparatuses (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operations steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical functions. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 6:
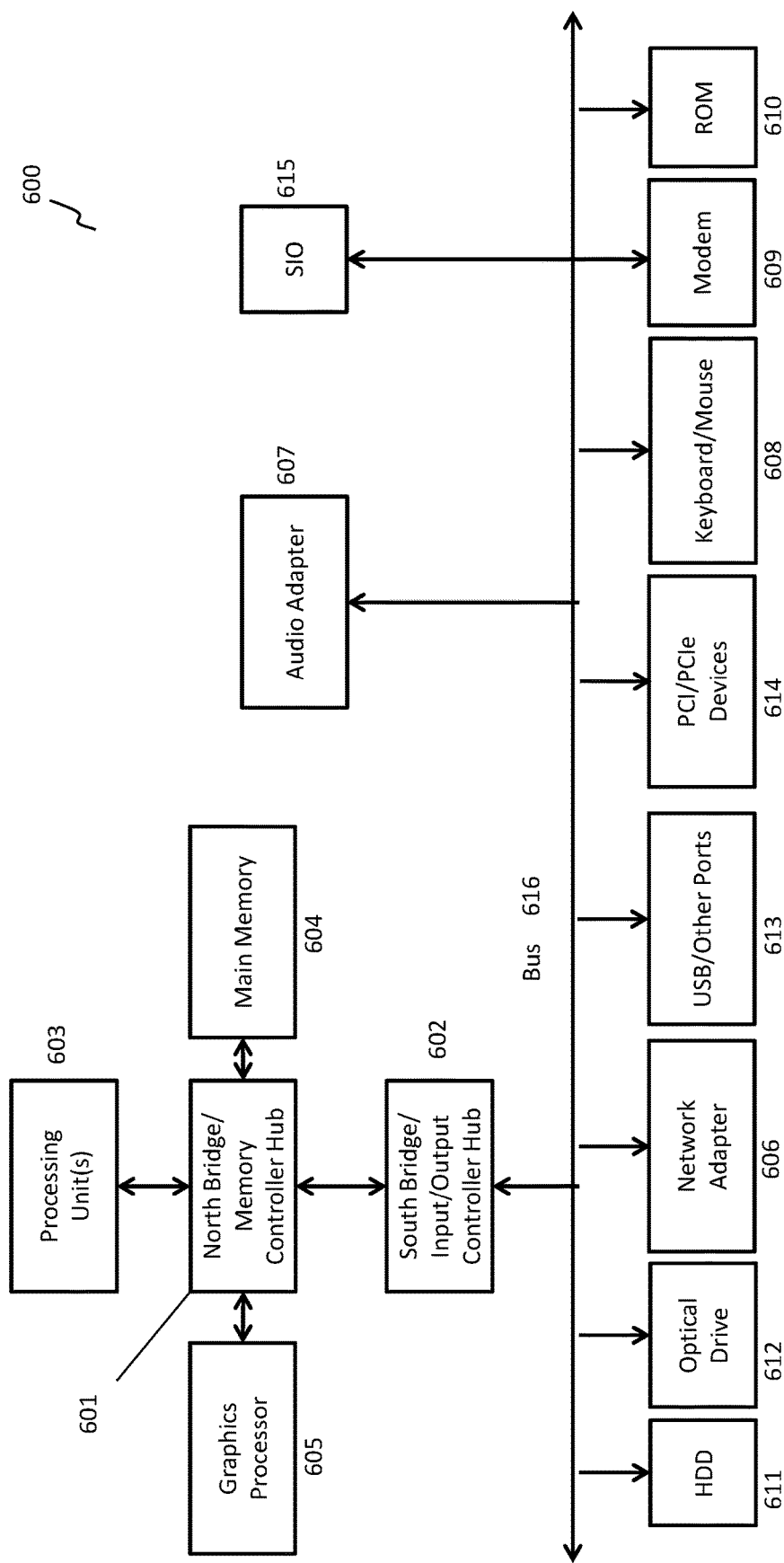
FIG. 6 depicts an illustrative computer system for performing processing of various embodiments.

FIG. 6 is a block diagram of an example data processing system 600 in which aspects of the illustrative embodiments are implemented. Data processing system 600 is an example of a computer, such as a server or client, in which computer usable code or instructions implementing the process for illustrative embodiments of the present invention are located. In one embodiment, FIG. 6 may represent a server computing device.

In the depicted example, data processing system 600 can employ a hub architecture including a north bridge and memory controller hub (NB/MCH) 601 and south bridge and input/output (I/O) controller hub (SB/ICH) 602. Processing unit 603, main memory 604, and graphics processor 605 can be connected to the NB/MCH 601. Graphics processor 605 can be connected to the NB/MCH 601 through, for example, an accelerated graphics port (AGP).

In the depicted example, a network adapter 606 connects to the SB/ICH 602. An audio adapter 607, keyboard and mouse adapter 608, modem 609, read only memory (ROM) 610, hard disk drive (HDD) 611, optical drive (e.g., CD or DVD) 612, universal serial bus (USB) ports and other communication ports 613, and PCI/PCIe devices 614 may connect to the SB/ICH 602 through bus system 616. PCI/PCIe devices 614 may include Ethernet adapters, add-in cards, and PC cards for notebook computers. ROM 610 may be, for example, a flash basic input/output system (BIOS). The HDD 611 and optical drive 612 can use an integrated drive electronics (IDE) or serial advanced technology attachment (SATA) interface. A super I/O (SIO) device 615 can be connected to the SB/ICH 602.

An operating system can run on processing unit 603. The operating system can coordinate and provide control of various components within the data processing system 600. As a client, the operating system can be a commercially available operating system. An object-oriented programming system, such as the Java™ programming system, may run in conjunction with the operating system and provide calls to the operating system from the object-oriented programs or applications executing on the data processing system 600. As a server, the data processing system 600 can be an IBM® eServer™ System p® running the Advanced Interactive Executive operating system or the Linux operating system. The data processing system 600 can be a symmetric multiprocessor (SMP) system that can include a plurality of processors in the processing unit 603. Alternatively, a single processor system may be employed.

Instructions for the operating system, the object-oriented programming system, and applications or programs are located on storage devices, such as the HDD 611, and are loaded into the main memory 604 for execution by the processing unit 603. The processes for embodiments described herein can be performed by the processing unit 603 using computer usable program code, which can be located in a memory such as, for example, main memory 604, ROM 610, or in one or more peripheral devices.

A bus system 616 can be comprised of one or more busses. The bus system 616 can be implemented using any type of communication fabric or architecture that can provide for a transfer of data between different components or devices attached to the fabric or architecture. A communication unit such as the modem 609 or the network adapter 606 can include one or more devices that can be used to transmit and receive data.

Those of ordinary skill in the art will appreciate that the hardware depicted in FIG. 6 may vary depending on the implementation. Other internal hardware or peripheral devices, such as flash memory, equivalent non-volatile memory, or optical disk drives may be used in addition to or in place of the hardware depicted. Moreover, the data processing system 600 can take the form of any of a number of different data processing systems, including but not limited to, client computing devices, server computing devices, tablet computers, laptop computers, telephone or other communication devices, personal digital assistants, and the like. Essentially, data processing system 600 can be any known or later developed data processing system without architectural limitation.

Figure 7:
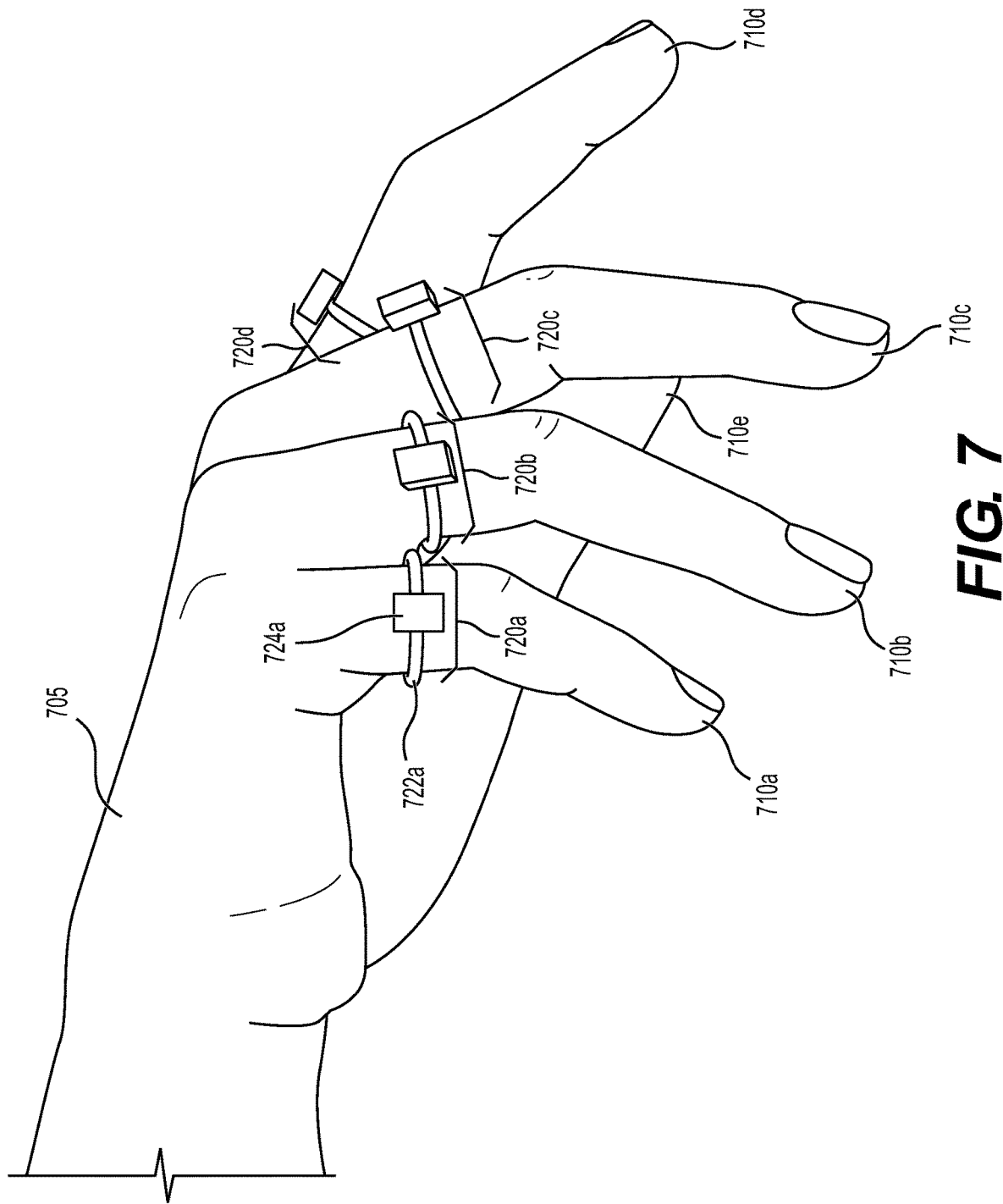
FIG. 7 depicts an embodiment of a disclosed system utilizing sensors on rings worn on the fingers of a hand.

FIG. 7 shows a user's hand 705 with digits 710*a-e*. In this example, several digits (as shown, digits 710*a-d*) are wearing a respective smart ring assembly 720*a-e*. Each smart ring assembly (as shown, smart ring assembly 720*a*) may contain a ring portion 722*a* and a sensor portion 724*a*.

Figure 8:
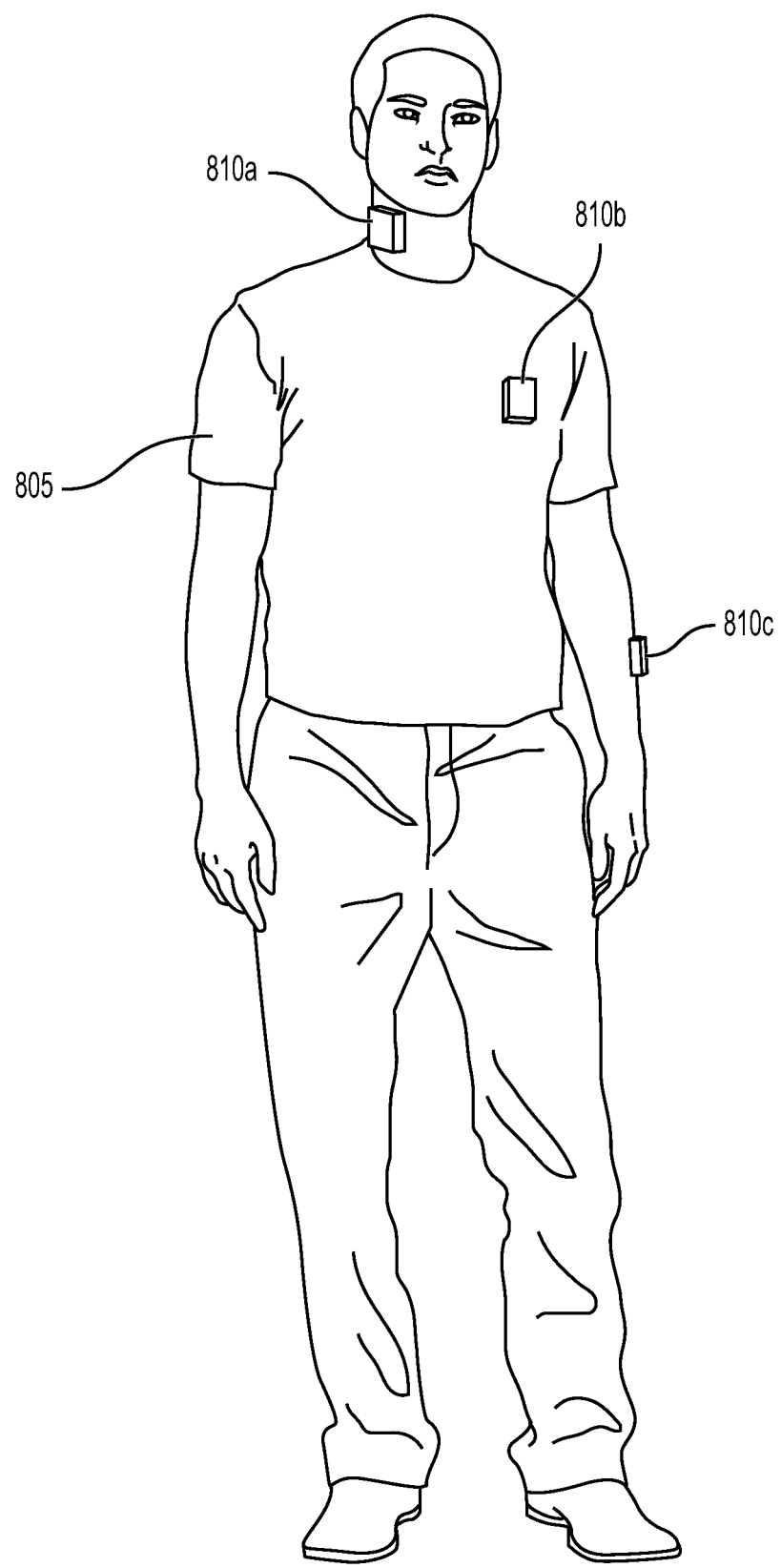
FIG. 8 depicts an embodiment of a disclosed system utilizing sensors placed on multiple body parts of a user.

FIG. 8 shows the user's human body 805. The user may be wearing one or more sensors (as shown, sensors 810*a*, 810*b*, and 810*c*) on various parts of the human body. For example, sensor 810*a* may be placed on the neck, sensor 810*b* may be placed on the chest, and sensor 810*c* may be placed on the forearm.

The system and processes of the figures are not exclusive. Other systems, processes, and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers, and processes can be implemented using hardware components, software components, and/or combinations thereof. No claim element herein is to be construed under the provisions of 35 U.S.C. 112(f) unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

The invention claimed is:

1. A wearable radiation detection system comprising:
   a housing;
   one or more pixelated imager chips located within the housing, each of the one or more pixelated imager chips being configured to operate as a direct detector, wherein the one or more pixelated imager chips comprise one or more of a photodiode, a color imager, a monochrome imager, a low light imager, an infrared imager, a thermal imager, a complementary metal-oxide-semiconductor imager, and a charge-coupled device imager; and
   one or more processors operably connected to each of the one or more pixelated imager chips, the one or more processors being configured to detect ionizing radiation using image data.

2. The wearable radiation detection system of claim 1, wherein the one or more pixelated imager chips are configured to acquire the image data without a scintillator.

3. The wearable radiation detection system of claim 2, wherein the image data comprises two-dimensional image data.

4. The wearable radiation detection system of claim 3, further comprising:
   one or more position sensors operably connected to the one or more processors and configured to acquire position data.

5. The wearable radiation detection system of claim 4, wherein the one or more processors are further configured to calculate a three-dimensional mass distribution based on the two-dimensional image data and the position data.

6. The wearable radiation detection system of claim 1, further comprising:
   one or more position sensors operably connected to the one or more processors and configured to acquire position data.

7. The wearable radiation detection system of claim 1, wherein the housing comprises one or more of a badge, a patch, a bracelet, a pendant, or a wrist computing device.

8. The wearable radiation detection system of claim 1, wherein the one or more processors are further configured to record a time stamp.

9. The wearable radiation detection system of claim 1, further comprising:
   a transmitter in operable communication with the one or more processors, wherein the one or more processors are further configured to cause the transmitter to wirelessly transmit the image data to a remote computing device.

10. The wearable radiation detection system of claim 1, further comprising:

one or more body temperature sensors configured to detect a temperature of a body of a user.

11. A wearable radiation detection system comprising:
a wearable housing;
one or more pixelated imager chips configured to operate as direct detectors and located within the wearable housing;
a processor operably connected to each of the one or more pixelated imager chips; and a non-transitory, processor readable storage medium operably connected to the processor, wherein the storage medium contains one or more instructions that, when executed, cause the processor to: receive image data from the one or more pixelated imager chips, and detect ionizing radiation based on the image data.

12. The wearable radiation detection system of claim 11, wherein:
the one or more pixelated imager chips comprise one or more of a photodiode, a color imager, a monochrome imager, a low light imager, an infrared imager, a thermal imager, a complementary metal-oxide-semiconductor imager, and a charge-coupled device imager; and
the one or more pixelated imager chips are configured to acquire the image data without a scintillator.

13. The wearable detection system of claim 11, wherein one or more pixelated imager chips comprise two or more pixelated imager chips positioned in two or more different orientations.

14. The wearable detection system of claim 13, wherein the two or more pixelated imager chips comprise a first pixelated imager chip of a first type and a second pixelated imager chip of a second type different from the first type.

15. The wearable detection system of claim 13, wherein the wearable housing comprises one or more of a badge, a patch, a bracelet, a pendant, or a wrist computing device.

16. A wearable radiation detection system comprising:
two or more pixelated imager chips configured to operate as direct detectors;
one or more processors;
memory in communication with the one or more processors and storing instructions that, when executed, are configured to cause the system to:
calibrate the two or more pixelated imager chips to detect radiation;
capture, using the two or more pixelated imager chips, image data in a manner controlled by the processor;
process the image data; and
detect radiation based on the processed image data.

17. The wearable radiation detection system of claim 16, wherein:
the two or more pixelated imager chips are positioned in two or more different orientations; and
the manner controlled by the processor is a long exposure image or video.

18. The wearable radiation detection system of claim 16, wherein the two or more pixelated imager chips are of two or more different types, and each of the two or more types of the two or more pixelated imager chips is calibrated differently.

19. The wearable radiation detection system of claim 16, wherein the radiation is detected in real-time, and the instructions are further configured to cause the system to trigger one or more of an alert indicative of detected radiation deviating from a threshold level or a notification indicative of a measured radiation dose rate.

20. The wearable radiation detection system of claim 16, wherein the two or more pixelated imager chips are positioned for wearing in two or more different locations on a body of a person.

* * * * *